(12) United States Patent
Samain et al.

(10) Patent No.: US 8,960,204 B2
(45) Date of Patent: Feb. 24, 2015

(54) COSMETIC METHOD FOR MODIFYING THE APPEARANCE OF THE CONTOUR OF THE EYE

(75) Inventors: Henri Samain, Bièvres (FR); Nathalie Jager Lezer, Verrières-le-Buisson (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/992,416

(22) PCT Filed: Dec. 7, 2011

(86) PCT No.: PCT/IB2011/055533
§ 371 (c)(1),
(2), (4) Date: Aug. 5, 2013

(87) PCT Pub. No.: WO2012/077074
PCT Pub. Date: Jun. 14, 2012

(65) Prior Publication Data
US 2013/0298931 A1    Nov. 14, 2013

Related U.S. Application Data

(60) Provisional application No. 61/442,484, filed on Feb. 14, 2011.

(30) Foreign Application Priority Data

Dec. 9, 2010  (FR) ..................... 10 60297

(51) Int. Cl.
*A45D 44/00*  (2006.01)
*A45D 44/22*  (2006.01)
(Continued)

(52) U.S. Cl.
CPC .............. *A45D 44/00* (2013.01); *A45D 44/002* (2013.01); *A61F 13/124* (2013.01); *A45D 44/22* (2013.01);
(Continued)

(58) Field of Classification Search
CPC ..... A45D 44/00; A45D 44/002; A45D 44/22; A61F 13/124; A61F 9/00718; A61F 2250/0059
USPC .......................... 132/200, 333, 320, 317, 319; 623/15.11, 15.12, 17.18; 606/204.25, 606/204.35, 5; 602/74, 54, 41; 424/401; 128/898
See application file for complete search history.

(56) References Cited

U.S. PATENT DOCUMENTS 2,001,862 A * 5/1935 Battey ...................... 606/204.35
2,572,638 A * 10/1951 Loos ............................ 128/858
(Continued)

FOREIGN PATENT DOCUMENTS

| CA | 1 199 847 | 1/1986 |
| FR | 2 538 247 | 6/1984 |
| WO | 01/34078 | 5/2001 |

OTHER PUBLICATIONS

Internal Search Report for corresponding International Patent Application No. PCT/IB2011/055533, dated Jan. 25, 2012.
(Continued)

*Primary Examiner* — Vanitha Elgart
(74) *Attorney, Agent, or Firm* — Jones Robb, PLLC (57) ABSTRACT

A cosmetic method for temporary modification of an appearance of a contour of an eye is disclosed. The cosmetic method comprises placing an aesthetic prosthesis at least on a hollow portion of an upper eyelid. The hollow portion is situated close to a medial canthus. The placing includes visually and/or physically filling at least a portion of the hollow portion with at least a first portion of the aesthetic prosthesis. An aesthetic filler prosthesis and a kit for an aesthetic filler prosthesis are also disclosed.

21 Claims, 3 Drawing Sheets

(51) Int. Cl.
*A61F 5/08* (2006.01)
*A61F 13/12* (2006.01)
*A61F 2/00* (2006.01)
*A61F 9/007* (2006.01)

(52) U.S. Cl.
CPC ........... *A61F 2/0059* (2013.01); *A61F 9/00718* (2013.01); *A61F 2210/0004* (2013.01); *A61F 2250/0059* (2013.01); *A61F 2250/0067* (2013.01)
USPC ..................................... 132/200; 606/204.35

(56) References Cited

U.S. PATENT DOCUMENTS

| | | | | |
|---|---|---|---|---|
| 2,862,509 | A * | 12/1958 | Porte | 132/53 |
| 3,266,500 | A * | 8/1966 | Weld | 132/53 |
| 3,485,251 | A * | 12/1969 | Brunet | 132/216 |
| 3,949,741 | A * | 4/1976 | Hofmann | 606/204.35 |
| 4,653,483 | A | 3/1987 | Clavin | |
| 4,854,307 | A | 8/1989 | Elfenbein | |
| 4,909,244 | A * | 3/1990 | Quarfoot et al. | 602/48 |
| 5,144,944 | A * | 9/1992 | Rice | 602/74 |
| 5,180,360 | A * | 1/1993 | Rhame, Jr. | 602/74 |
| 5,496,370 | A * | 3/1996 | Hamas | 623/23.67 |
| 5,728,157 | A * | 3/1998 | Prescott | 424/423 |
| 5,887,590 | A * | 3/1999 | Price | 128/858 |
| 6,190,346 | B1 | 2/2001 | McGill | |
| 6,193,740 | B1 * | 2/2001 | Rodriguez | 606/204.25 |
| 6,193,741 | B1 * | 2/2001 | Heavenridge et al. | 606/204.35 |
| 6,733,856 | B2 * | 5/2004 | Nojiri | 428/40.1 |
| 7,066,182 | B1 * | 6/2006 | Dunshee | 128/888 |
| 7,608,090 | B2 * | 10/2009 | Matsui | 606/204.35 |
| 8,282,684 | B2 * | 10/2012 | Aray | 623/17.18 |
| 2002/0198597 | A1 * | 12/2002 | Godfrey | 623/15.11 |
| 2003/0204159 | A1 * | 10/2003 | Lawry | 602/48 |
| 2004/0074502 | A1 * | 4/2004 | Abbasi | 128/858 |
| 2004/0138699 | A1 * | 7/2004 | Lish | 606/204.35 |
| 2005/0257805 | A1 * | 11/2005 | Williams | 132/320 |
| 2006/0115519 | A1 | 6/2006 | Matsui | |
| 2006/0217813 | A1 * | 9/2006 | Posnick et al. | 623/17.18 |
| 2007/0067041 | A1 * | 3/2007 | Kotoske | 623/17.18 |
| 2009/0234382 | A1 * | 9/2009 | Dillon | 606/204.35 |
| 2009/0272394 | A1 * | 11/2009 | Livacich et al. | 132/200 |
| 2010/0218783 | A1 * | 9/2010 | Dobler et al. | 132/320 |
| 2010/0282269 | A1 * | 11/2010 | Uchida et al. | 132/200 |
| 2011/0034849 | A1 * | 2/2011 | Cooks | 602/74 |
| 2011/0271973 | A1 * | 11/2011 | Iwagaki et al. | 132/200 |
| 2012/0239079 | A1 * | 9/2012 | Cohen et al. | 606/204.25 |
| 2013/0089584 | A1 * | 4/2013 | Jager Lezer et al. | 424/401 |
| 2013/0125911 | A1 * | 5/2013 | Mammone | 132/200 |
| 2013/0125912 | A1 * | 5/2013 | Tojo et al. | 132/200 |
| 2013/0146076 | A1 * | 6/2013 | Dunaway | 132/200 |
| 2013/0247928 | A1 * | 9/2013 | Valucci et al. | 132/200 |

OTHER PUBLICATIONS

Written Opinion of the International Searching Authority for corresponding International Patent Application No. PCT/IB2011/055533, dated Jan. 25, 2012.
French Preliminary Search Report for corresponding French Patent Application No. FR1060297, dated May 13, 2011.
French Written Opinion for corresponding French Patent Application No. FR1060297, dated May 13, 2011.
Machine Translation of French Patent Document No. FR 2538247, original document dated Jun. 29, 1984.

* cited by examiner

COSMETIC METHOD FOR MODIFYING THE APPEARANCE OF THE CONTOUR OF THE EYE

CROSS REFERENCE TO RELATED APPLICATIONS

This is a national stage application of PCT/IB2011/055533, filed internationally on Dec. 7, 2011, which claims priority to U.S. Provisional Application No. 61/442,484, filed on Feb. 14, 2011, as well as French Application No. FR 1060297, filed on Dec. 9, 2010, the entire contents of each of which is incorporated herein by reference

FIELD OF THE INVENTION

The present invention relates to a cosmetic method for modifying the appearance of the contour of the eye and associated aesthetic prosthesis and kit.

Many people wish to modify the appearance of the contour of their eyes, notably in order to make them look more beautiful, for example according to recognized or personal aesthetic criteria, in order to change the appearance of their looks or else to correct one or more imperfections, for example a scar.

Some people, notably of Caucasian type, experience a hollowing of the upper eyelid. The hollow may be visible mainly at the inner eye corner. This is then called a cavity or a recess when the hollow takes a more elongate shape. In both cases, the hollow does not necessarily result from the effect of age but marks an ageing effect and, because of this, is disliked. The deeper the cavity or recess the more apparent the phenomenon on account of shadow play that these reliefs produce.

For other people, the hollow is not very marked per se, but becomes clearly visible because of an asymmetry between the two eyes; a difference, however slight, gives an unattractive appearance.

Finally, some people may also wish to modify the shape of the contour of their eyes because of their dimensions, one eye for example being too closed or too open, too large or too small, or having an undesirable bulging appearance.

BACKGROUND

It is known practice to apply make-up products to the contour of the eye, notably in order to make it possible to emphasize by the colours all or some of the contour of the eyes. However, making up the eyes has several drawbacks. It makes it possible to make the eye stand out but does not deal with the shape of the contour of the eyes. It is in particular difficult to rectify asymmetries and virtually impossible to rejuvenate an appearance. Moreover, the shadow play created by make-up does not suit a large number of people, notably men, children, old people and certain women. Make-up also requires adequate expertise for applying it effectively. Moreover, it is often necessary to take certain precautions to maintain the result of make-up over time, notably by avoiding any rubbing or washing, and since make-up usually lasts only a few hours, or even a day or two, it is necessary to repeat it regularly.

It is known how to modify the looks of a person by the use of cosmetic surgery. However, most people prefer not to use it, since this solution is often considered too radical and sometimes painful. Moreover, cosmetic surgery cannot be reversed, is suitable most of all for quite important corrective purposes and is not suitable for minor corrective purposes or for satisfying the simple desire to temporarily change the appearance of the eyes.

U.S. Pat. No. 4,854,307 describes the application of a liquid adhesive compound in order to stick together the upper moving eyelid and the upper fixed eyelid of the eye. Sticking has the drawback of being uncomfortable and dangerous for the user and does not allow a correction or a modification of the appearance that is precise and suitable for each user.

U.S. Pat. No. 6,190,346 and application WO 01/34078 describe the application of an adhesive flat strip to the movable portion of the upper eyelid in order to correct the collapse of the eyelid. This solution does not make it possible to correct or modify the contour of the eye as effectively and comfortably as is desired, the strip not being suitable for the topology of the eyelid to which it is applied.

U.S. Pat. No. 4,653,483 describes an adhesive strip designed to be applied to the movable upper eyelid of the eye in order to carry out pseudo blepharoplasty.

There is a need to remedy at least some of the above-mentioned drawbacks.

It is notably desirable to be able to modify the appearance of the contour of the eye in an attractive, simple, durable, effective, reversible manner and in a way that is suitable for all types of eyes, whether they be Caucasian, Asiatic or African and of all ages.

BRIEF SUMMARY

The subject of the invention is therefore, according to one of its aspects, a cosmetic method for the temporary modification of the appearance of the contour of the eye, comprising the placing, at least on a hollow portion of the top eyelid situated close to the medial canthus, of an aesthetic prosthesis comprising at least a first portion capable of filling, visually and/or physically, at least partially the said hollow portion.

BRIEF DESCRIPTION OF THE DRAWINGS

The invention will be better understood on reading the following detailed description of non-limiting exemplary embodiments of the latter, and by examining the figures of the appended drawing, the said figures being schematic and partial, in which.

DETAILED DESCRIPTION OF THE INVENTION

The subject of the invention is therefore, according to one of its aspects, a cosmetic method for the temporary modification of the appearance of the contour of the eye, comprising the placing, at least on a hollow portion of the top eyelid situated close to the medial canthus, of an aesthetic prosthesis comprising at least a first portion capable of filling, visually and/or physically, at least partially the said hollow portion.

By "visually fill" it should be understood that the first portion covers the hollow portion which is therefore no longer visible.

By "physically fill", it should be understood that the first portion occupies the space defined by the concavity of the hollow portion.

The aesthetic prosthesis according to the invention is an object of predefined or adaptable shape.

The prosthesis that is applied in the medial hollow of the eye must be able to stick to the skin and camouflage the hollow, for example by closely following the shape of the hollow.

The canthus is the indentation situated at each corner of the eye, at the ends of the palpebral aperture. The medial canthus, or large canthus, is situated on the nose side and the lateral canthus, or small canthus, is close to the temporal region of the skull. In Caucasian or African people, the lateral canthus is more rounded.

The maximal thickness of the first portion, once this is in place with its final shape, measured between the application face, that is to say the face turned towards the skin and the outer face, opposite to the application face, may be greater than or equal to 300 µm, or even 500 µm, notably between 500 µm and 5 mm.

The first portion may comprise a malleable material, for example flexible to semi-rigid, that may be forced in situ to take the shape of the hollow portion, for example a cellular material such as an aerogel which can be squashed. This material therefore makes it possible, by pressure, to obtain the desired shape. The material may be sufficiently malleable for the user to be able to adapt its shape to his morphology during application. As a malleable material suitable for the invention it is possible to cite the modelling compounds, for example consisting of a mixture of oil, corn starch, flour and aluminium potassium sulphate, the mastics notably mixtures of wax, oil and resin, with or without additional mineral powder, the pasty mixtures obtained notably by mixing organic or mineral powder, organic or mineral fibres with water or organic solvents, in particular non-volatile solvents, this list being non-limiting.

In one variant, the first portion is made of non-malleable material, for example elastic, semi-rigid or rigid, with a predefined shape. The first portion may then be chosen or made according to the morphology of the person, and even made-to-measure, in order to be adapted to the shape of the hollow portion, so that all that remains is to put it in position in order to have the desired effect.

As a variant, the first portion may comprise a cavity which may or may not be closed and may or may not be hermetic. This cavity may be filled, at least before the prosthesis is placed on the hollow portion, with a gaseous or liquid fluid compound. The first portion may be solid.

The first portion, even with no cavity, may comprise a fluid compound, at least before the prosthesis is placed in the hollow portion.

The fluid compound is preferably pasty, and has characteristic rheological parameters comprising the yield point, the modulus of elasticity and the modulus of viscosity, as defined below.

The structural breakdown stress point or yield point $\tau_0$ of pasty compounds is defined as being the pressure necessary to cause a macroscopic flowing of the pasty compound; it may be determined by carrying out a stress test, for example with the aid of an imposed stress Haake rheometer RS150 at a temperature of 25° C.

Moreover, the modulus of elasticity and the modulus of viscosity of the pasty compounds may be measured for a stress frequency of 1 hertz in the zone called the linear viscoelasticity zone defined by the fact that the stress applied during the measurement is less than the structural breakdown yield point of the pasty compound.

Usually, the pasty compounds according to the invention are characterized by a modulus of elasticity, at 25° C., that is greater than 5,000 Pascals and preferably greater than 10,000 Pascals, and a tangent value ($\delta$) given by the ratio of the modulus of viscosity over the modulus of elasticity, below 0.2, at 25° C. for a stress frequency of 1 hertz.

The yield point of the pasty compounds according to the invention is greater than 50 Pa·s or preferably greater than 100 Pa·s.

The viscosity of the pasty compounds according to the invention is equal to or greater than 5000 Pa·s for a shear rate equal to $10^{-3}$ $s^{-1}$ and preferably greater than 10,000 Pa·s and notably less than 10,000,000 Pa·s, viscosity measured at 25° C. with a Haake Rheostress RS 150 apparatus in cone and plate configuration.

The fluid compound, for example inside the cavity, may be reticulatable and notably reticulated in situ. It is possible to cite as an example the polysaccharides of the alginate type, oxidized starch, reactive silicones, cyanoacrylates, reticulatable latexes, with zinc for example.

Preferably, once the prosthesis is in place and after possible reticulation, it retains a certain flexibility, or even elasticity. Thus, the Young's modulus of the material of the prosthesis in place in the hollow portion is preferably below 50 MPa, or even below 1 MPa.

In one variant, the fluid compound contained in the first portion of the prosthesis or forming the first portion of the prosthesis, and which is preferably pasty, changes in rheology so as to lose its deformability a few minutes after the prosthesis is put in place. This change may be the result of a chemical or physical reaction triggered naturally or intentionally. In particular, it is possible to mix extemporaneously two compounds, which cause a reticulation for example. This change may also be the result of an evaporation or elimination of a solvent of the compound. In particular, the fluid compound may be chosen so that a slight evaporation of the solvent produces a marked increase in density. The fluid compound may therefore contain a powder and a binder, with or without volatile solvent.

The prosthesis may comprise an object that is applied in the hollow portion and covered by the preferably pasty fluid compound, or the reverse.

The first portion of the prosthesis may comprise an elastic, semi-rigid, or rigid object pre-coated with a pasty fluid compound on one or the other of its two faces.

First and Second Portions of the Prosthesis

The prosthesis may be local and be limited to the first portion with the aim of filling at least partially the hollow portion. The first portion is then indistinguishable from the complete prosthesis.

In another exemplary embodiment, the prosthesis is more extensive and comprises a second portion which extends beyond the hollow portion, for example over a larger portion of the movable upper eyelid, or even over the whole movable upper eyelid, or even passes beyond to the fixed portion of the upper eyelid.

The second portion of the prosthesis does not, by definition, participate in the filling of the hollow portion. The second portion may help to maintain the prosthesis in its entirety over time, and to also modify the appearance of the eye.

The second portion is for example connected to the first portion by an articulation. The articulation may help the placing of the prosthesis and, once the second portion is in place on the movable portion of the eyelid, make mobility easier relative to the first and second portions. This articulation may be a zone of reduced thickness between the first and second portions, corresponding for example to an increased zone of deformability, or a fold. In one variant, the articulation is a bridge of material connecting the first and the second portions. The second portion may also be detachable from the first portion or degradable, notably by dissolving in a solvent.

In one variant, the second portion comprises an articulation so as not to hamper the mobility of the movable upper eyelid.

The first portion, capable of filling at least partially the hollow portion of the upper eyelid situated close to the medial canthus, may also comprise an articulation, for example a fold of a membrane placed on the hollow portion of the eye corner.

The prosthesis may comprise a guidance portion extending, at least during a step of placing the prosthesis, over the whole eyelid and/or a portion of the nose.

The guidance portion may then be detached from the prosthesis.

The prosthesis is for example situated on the internal, slightly adhesive face of a long strip, forming the guidance portion. It is placed on the base of the nose in its first end, superposed on the first portion, then it is applied by pressing it gradually until the lateral canthus is reached corresponding to the outer corner of the palpebral fold.

Finally, the strip is removed. The prosthesis remains stuck to the eyelid. The value of this strip is that it correctly situates the assembly in order to have an easy, precise and possibly symmetrical application because it is then sufficient to carry out the same operation to place the second prosthesis on the second eyelid.

In one variant, the prosthesis has a space between the first and the second portion and/or the second portion comprises several portions spaced apart. The prosthesis thus delimits the intermediate zones where the skin is not covered. The interval or intervals thus created prevent the second portion from having folds during certain movements of the muscles of the movable upper eyelid which fold the skin, in particular in certain mimics. Before the placement on the eyelid, the first portion and the portions forming the second portion are positioned precisely on the guidance portion depending on the arrangement and the desired gaps. The prosthesis is then placed on the eyelid as explained above.

The prostheses for both eyes may or may not be symmetrical. In particular, in the case of prostheses comprising several spaced portions, the gaps formed and the relative positioning of the various portions do not have to be symmetrical. For one and the same patient, it is possible in particular to produce only one prosthesis, without the other eye also requiring a prosthesis.

Material of the Prosthesis

The prosthesis is made so as not normally to cause irritation to the skin and the eye. It therefore has no sharp edge or point likely to injure the user.

The first and/or possibly the second portion of the prosthesis may comprise at least one polymer, or other synthetic material, chosen from:

a polyolefin, notably polyethylene, polypropylene, polyisoprene, polystyrene, polybutadiene, polyacrylate, polyacrylamide, a polymer originating from condensation reactions, for example a polyester, polyurethane, polyamide, polyurea, polyamide/polyether copolymer, another organic or organomineral polymer, for example polyether, silicone, a natural polymer such as a polyose (for example cellulose), a protein, a wax, amongst others.

The first and/or possibly the second portion of the prosthesis may comprise a mineral and/or metallic material, chosen from:

an oxide, carbide, nitride, carbonate, phosphate, metal sulphate, alkaline earths, alkaline, for example calcium carbonate or calcium phosphate, silicate, aluminosilicate, ceramics, metal or alloy, based on iron, aluminium, titanium, magnesium, silver, gold or platinum, amongst others.

The first and/or possibly the second portion of the prosthesis may comprise a material comprising natural fibres, a fabric or other woven form, a paper or other non-woven form, wood, biocellulose, amongst others.

The first and/or possibly the second portion of the prosthesis may be made of a pure material or mixed with another material.

The first portion may be made of a material that is more flexible than the rest of the prosthesis, notably in order to allow a more easy placement in the hollow portion of the corner of the eye and/or on the opposite end of this hollow portion.

The first portion may or may not be made of the same material as the rest of the prosthesis.

The rigidity of the prosthesis may be between 200 kPa and 200 GPa, preferably between 1 MPa and 10 GPa, or even between 5 MPa and 4 GPa.

The first and/or the second portions may contain a solvent such as water or a volatile solvent or a non-volatile solvent. The first and/or the second portions may contain a plasticizer or a non-volatile solvent which, in contact with the skin, will be absorbed by the skin. Thus, the first and/or the second portions may be fairly flexible, or even take the form of a gel, then remain in this form, or change in order to become more rigid.

The first and/or the second portion may be proposed in a form in which the user must cut it and/or fashion it before applying it. The first portion and/or the second portion is for example supplied via a dispenser roll.

The prosthesis may have a rigidity and/or a thickness that are variable in order, for example, to be more easily fixed and to better adapt to the shape of the hollow portion. The thickness of the prosthesis and/or the rigidity of the prosthesis may be variable along at least one axis of the prosthesis, for example the longitudinal axis of the prosthesis or along an axis perpendicular or oblique relative to the longitudinal axis of the prosthesis. The prosthesis may have an elasticity that can vary depending on the position on the prosthesis associated, for example, with a variation in the thickness of the prosthesis.

The rigidity of the prosthesis, between at least two zones of the prosthesis, may vary at least by a factor 2, for example at least a factor 5. The thickness of the prosthesis between at least two zones of the prosthesis may vary at least by a factor 1.25, for example at least a factor 2.

When the rigidity of the prosthesis is variable, the difference in rigidity is for example obtained by the use of at least two materials of different rigidities, by the addition of at least one reinforcing element, by a difference in concentration in at least one compound of the prosthesis and/or by a difference in treatment between at least two zones of the prosthesis.

The thickness of the prosthesis may also be variable and the rigidity of the prosthesis constant.

The prosthesis may comprise a non-homogenous material comprising notably particles, fibres, small plates or vacuoles, voids, and/or trapped or connective bubbles.

The prosthesis, and notably at least the first and/or the second portion, may be porous to oxygen, air and to water vapour in order to allow the eyelid to breath.

Membrane

The prosthesis, for example the first or the second portion, may comprise at least one membrane, preferably elastically deformable.

The membrane may have an elasticity that varies depending on the location, associated, for example, with a variation in the thickness of the membrane.

The membrane may be thinner and/or less rigid in the central portion than on the edges of the membrane, notably at the longitudinal ends of the membrane. As a variant, the membrane may be thicker and/or more rigid in the central portion than at the edges of the membrane, notably at the longitudinal ends of the membrane.

The thickness and/or the rigidity of the membrane may vary in a monotonic manner, for example decreasing or increasing, from one end to the other of the membrane or from the middle to the longitudinal ends of the membrane.

The membrane may have periodic or irregular variations in thickness and/or in rigidity from one end to the other of the membrane, notably from one longitudinal end to the other.

The membrane may have at least one localized zone with a thickness and/or rigidity that differs from the rest of the membrane, notably from one longitudinal end to the other.

Typically, when the prosthesis comprises a membrane, the thickness of the membrane is between 10 μm and 1 mm, preferably between 5 μm and 200 μm.

The first portion of the prosthesis may comprise a membrane superposed on a malleable or non-malleable material.

The membrane may be placed on the hollow portion of the corner of the eye after application of a fluid, preferably pasty, compound in the hollow portion.

The membrane may have sticking edges to help to attach it to the skin.

The first portion may comprise a first and a second elastic membrane and a malleable or non-malleable material placed between the membranes.

Adhesion of the Prosthesis on the Skin

The prosthesis is made so as to be able to adhere to the skin, being designed to remain for a few hours, for example throughout a daytime, or to remain for several days.

The prosthesis has both an application face that must be able to adhere to the skin and an outer face.

The application face of the prosthesis and/or the movable upper eyelid may be covered at least partially with a compound making it easier for the prosthesis to adhere to the movable upper eyelid. This compound may be chosen in particular from the resins, adhesives, notably pressure-sensitive adhesives (PSA), reactive materials.

This compound may be applied before the prosthesis is placed on the eyelid and/or on the prosthesis. The compound may be applied by the user if necessary. The compound may also be present on the prosthesis when the latter is supplied to the user.

The prosthesis may also comprise, if necessary, a non-adhesive portion defining at least partially the application face.

The compound allowing the adhesion of the prosthesis to the eyelid may be non-adhesive, being for example a gel, a cream, a solvent or an oil, and may or may not comprise an active agent, making it possible to give the prosthesis a sufficient adhesion through the effect of forces of capillarity.

The compound may, if necessary, cover certain zones only of the application face of the prosthesis and/or of the movable upper eyelid, for example the zones situated on the border of the prosthesis and/or of the movable upper eyelid.

The hold of the prosthesis may also be improved by the choice of the material of its application face. For example, the application face of the prosthesis may be covered with an anti-skid material, preferably an elastomer.

The use of a first portion comprising a reticulatable pasty material provides a certain adhesion. However, in order to enhance it, the reticulatable pasty compound may comprise an additional adhesive, in particular if the rheology of the pasty compound does not change once the latter has been applied.

Preferably, the prosthesis can be held in place with the aid of an adhesive having a low adhesive power, or even without the use of adhesive, for example by a simple surface tension, which makes the prosthesis easier to remove, allows less irritation of the skin and/or an easier repositioning of the prosthesis on the hollow portion of the contour of the eye. Thus, in certain exemplary embodiments, the prosthesis is not or not very sticky when it is ready to be applied, notably after the pasty compound has reached its final rheology.

Preferably, at least one surface of the prosthesis is adhesive. For example, the prosthesis may comprise an adhesive surface in contact with the skin, or, in another example, the first portion comprises a membrane superposed on an adhesive surface of the object.

The adhesive compound making for easier adhesion of the prosthesis that is applied, where necessary, on the movable upper eyelid, may react with at least one material in which at least one portion of the prosthesis is made. The compound applied to the movable upper eyelid may for example be a silicone with reactive functions such as those of hydrosilylation or a cyanoacrylate monomer.

The method according to the invention may include the application of a material limiting the final adhesion on the outer surface of the prosthesis. In particular, it is possible to apply to the visible face of the prosthesis, opposite to the application face, a greasy liquid, a powder, or a polymeric coating.

Make-Up-Visual Appearance

The prosthesis may be placed on the bare skin or on the prepared skin. The prosthesis may be coloured and/or textured. It is possible to cover the prosthesis with a film or a make-up.

The application face of the prosthesis, and/or the outer visible face, may confer a soft and smooth appearance, close to that of the skin. It may be smooth or have a roughness, cavities and/or asperities.

The visible outer face of the prosthesis may simulate the human skin, notably the skin of the eyelid. In particular, it may have the same colour, the same texture and/or the same relief as the skin of the eyelid before application, or as a reference skin, satisfying, for example, certain aesthetic criteria.

The prosthesis may be coloured or uncoloured, monochrome or multicoloured. The prosthesis preferably has a colour close to that of the human skin and/or is partly transparent and/or translucent, making it possible to observe the skin of the eyelid through the prosthesis. The prosthesis may thus make it possible to modify the appearance of the contour of the eye while being virtually invisible to the eyes of an observer.

The prosthesis may have a shiny or matt effect. A shininess may provide an aesthetic effect of the prosthesis, notably for young people, while a matt aspect may provide the prosthesis with greater discretion, notably for older people.

The state of the surface of the visible outer face of the prosthesis may be sufficiently rough to allow an eyelid make-up product to adhere.

If necessary, the prosthesis is supplied to the user with at least one make-up product compatible with the application on the outer face of the prosthesis, this make-up product being for example initially contained in one and the same package as the prosthesis.

Removal of the Prosthesis

It is possible to remove the first and/or the second portion by scratching it, or softening it, at least partially or limiting the adhesive strength by the addition of a third component, for example water.

In the case of a prosthesis comprising a second portion, it is possible for example to remove first this second portion and then use it, for example by pulling it lightly, to unstick the first portion.

Presence of Active Agent

The prosthesis may have no active agent or, on the contrary, facilitate the application of an eye-care or eyelid-care active agent, and make comprise such an active agent. In particular, the prosthesis may be used as a reservoir for the application of a cosmetic product on the movable upper and/or fixed eyelid. The prosthesis may for example be made of or comprise a porous material impregnated with an active agent. The prosthesis may for example allow the release of a cosmetic active agent for the care or the growth of the eyelashes, for example some bimatoprost, for an anti-ageing treatment of the eyelid, in order to provide comfort for the eye, for example with the aid of water, a physiological liquid, an anti-irritation active agent, an anti-dust active agent, amongst others. The active agent applied may be cosmetic with no therapeutic action.

The active agent may be incorporated into the prosthesis before the latter is put in place and/or incorporated into the prosthesis at the time that it is put in place and/or after it is put in place. The active agent may be incorporated into the prosthesis with or without solvent.

When the prosthesis contains an active agent, the prosthesis may be proposed to the user in a hermetic, for example sterile, package.

A further subject of the invention, independently of or in combination with the foregoing, is an aesthetic filler prosthesis comprising a first preformed portion with a shape corresponding to that of a hollow portion of the upper eyelid, situated close to the medial palpebral canthus. The prosthesis may have all or some of the features specified above considered in isolation or in combination.

A further subject of the invention, independently of or in combination with the foregoing, is a kit for an aesthetic filler prosthesis comprising:

a malleable material or a receptacle containing a fluid compound that is pasty and/or reticulatable and, a membrane to be applied partly to the eyelid in order to hold the malleable material or a certain quantity of the compound in position.

The membrane may be applied as is. In a variant, the user may cut the membrane to the appropriate shape and dimensions. This cutting can be carried out manually or automatically, for example based on a 2D or 3D snapshot of the eyelid including the hollow portion to be filled.

The membrane may consist of an adhesive film that can be cut.

The membrane can keep in place a quantity of the composition between 1 mg and 100 mg, preferably between 5 mg and 50 mg.

Figures 1A, 1B, 2, 3A, 3B, 3C:
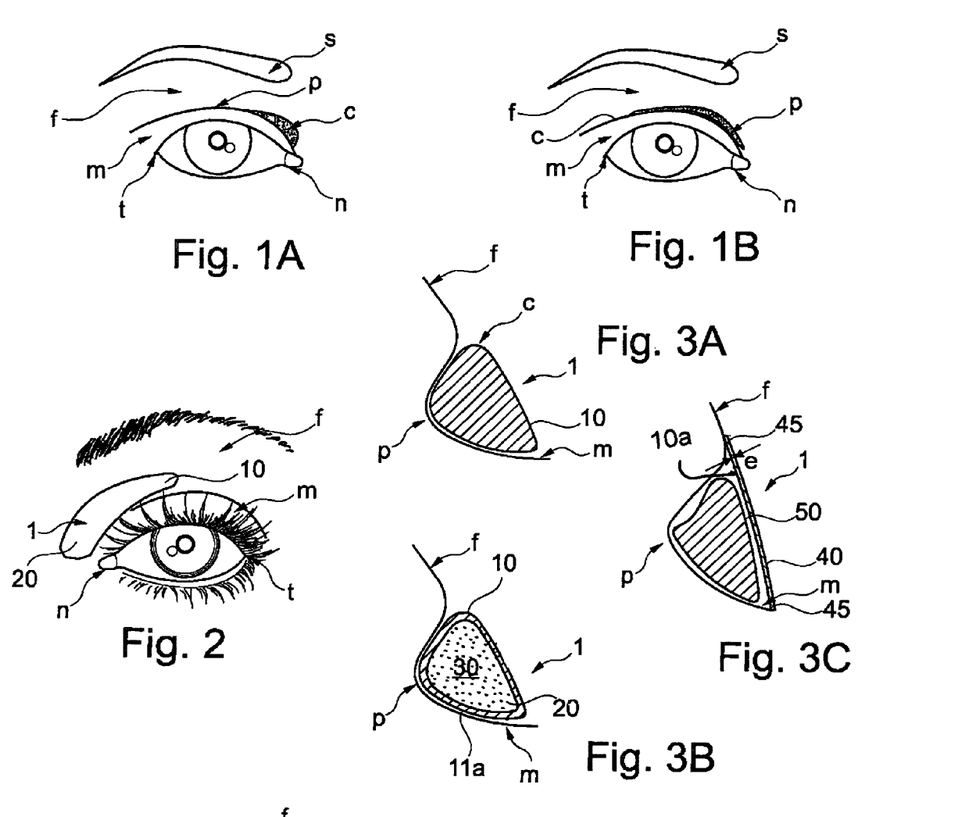
FIGS. 1A and 1B represent respectively a cavity and a recess at the medial canthus and the palpebral fold.
FIG. 2 shows from the front a first exemplary embodiment of a prosthesis according to the invention placed in the hollow portion of the eye.
FIGS. 3A to 3C represent in section the hollow portion with various prostheses made according to the invention.

FIG. 1A shows various elements that are characteristic of a right eyebrow s, including the fixed upper eyelid f, the palpebral fold p, the movable upper eyelid m, the nasal or medial canthus or large canthus n and the temporal or lateral canthus t, at the ends of the palpebral aperture. In the example illustrated, the eye has a hollow portion c situated close to the nasal canthus n corresponding to the end of the palpebral aperture situated on the side of the nose.

The hollow portion c forms a cavity that can be seen mainly in the corner of the eye. The depth of this cavity may reach a millimeter or more, and the cavity is seen notably due to the shadow that is cast and by the texture of the skin which may be different. This type of hollow portion c is encountered in particular on people having an eyebrow s that is fairly highly placed relative to the eye.

In FIG. 1B, the sunken element that partly follows the palpebral fold is called a recess and takes a more elongate shape, for example because of an eyebrow s that is not very high relative to the eye, but remains as visible as in the previous case.

In general, the prosthesis comprises at least one portion, called the first portion that adapts to the shape of the hollow portion situated close to the medial canthus n.

In certain exemplary embodiments, for example corresponding to the presence of an additional recess of the hollow portion as illustrated in FIG. 1B, the prosthesis may be extended and comprise a second portion. For greater clarity in the rest of the description, mention will be systematically made of the first portion for the portion of the prosthesis covering the hollow portion, even in the absence of a second portion. For example, the prosthesis shown from the front in FIG. 2 is a local prosthesis comprising a single first portion 1, stuck to the hollow portion of the medial corner of the eye bordering the ridge of the nose.

The prosthesis and the upper eyelid may be made up after the prosthesis is placed, the hollow portion and the prosthesis becoming not very visible or not at all visible.

FIG. 3A shows the hollow portion c above the medial canthus of the eye n, filled with the aid of a prosthesis 10 according to the invention. The prosthesis illustrated comprises a solid first portion 1 made of a malleable material, for example a mixture of talc and oleic acid.

FIG. 3B represents another prosthesis 10 according to the invention. The prosthesis is local and limited to a first portion 1 comprising a cavity 30. The first portion 1 is made for example of polyamide and the cavity is filled for example with a fluid 20, for example formed by a guar gum notably marketed under the name Jaguar® HP105 by the company RHODIA diluted to 4% in water. The cavity 30 is non-hermetic and, when the first portion 1 is put in place, the user may, by pressing the prosthesis 10, cause the excess fluid to come out and thus give the first portion 1 the desired volume. The application face 11a of the prosthesis is covered with adhesive which allows it to be attached in order to fill the hollow portion.

In the exemplary embodiment illustrated in FIG. 3C, the prosthesis comprises a first portion 1, that is solid and formed of an object 50 made of a malleable material, and a membrane 40 covering the object 50 made of a malleable material and the edges 45 of which are in contact with the skin. When the user installs the malleable material 50, he squashes it in order to give it the shape of the hollow portion c to be filled. The membrane 40 then makes it possible to give a smoother external appearance to the prosthesis.

The user may place the membrane 40 after having cut it to the desired dimensions.

The application face 10a of the membrane 40, turned towards the hollow portion to be filled, is adhesive. In its central portion, the membrane 40 is thus stuck to the malleable material 50, the edges 45 of the membrane being stuck to the skin, in particular to the fixed upper eyelid and the movable upper eyelid, in order to help the attachment of the prosthesis.

In a variant not illustrated, the membrane 40 comprises edges 45 turned inwards in order to make it easier to attach to the skin.

The membrane 40 may be made of polyamide, polyurethane or polyamide/polyether copolymer.

The thickness of the membrane 40 is for example between 10 µm and 1 mm.

Figure 4A:
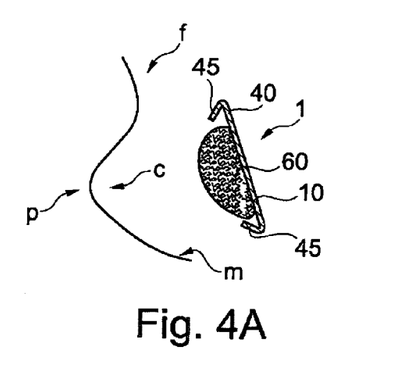
FIGS. 4A and 4B illustrate various embodiments of the first portion of the prosthesis.
Figure 4B:
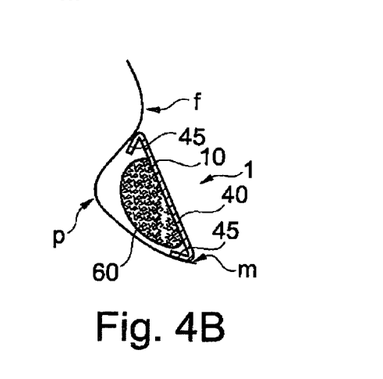

FIG. 4A shows, before the placement and cutting, a prosthesis 10 comprising a membrane 40 covering a mass of pasty fluid compound 60. The prosthesis is positioned on the hollow of the eyelid as illustrated in FIG. 4B. The membrane 40 may comprise edges 45 turned inwards which adhere to the skin by a phenomenon of mechanical tension.

The membrane 40 may have a thickness e which may or may not be constant.

Figure 5:
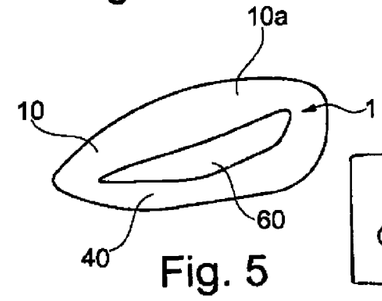
FIG. 5 shows another exemplary embodiment of a prosthesis according to the invention.
Figure 11:
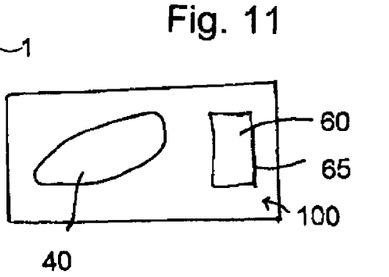
FIG. 11 shows an example of a kit for an aesthetic filler.

The example illustrated in FIG. 5 shows, seen from the side of the application face 10a, a first portion 1 of a local prosthesis 10. The first portion comprises a membrane 40 on which a pasty compound 60 has been placed on its adhesive portion serving as the application face. FIG. 11 shows for example the membrane 40 and a receptacle 65 of the pasty compound 60 in a kit 100.

Figures 6, 7:
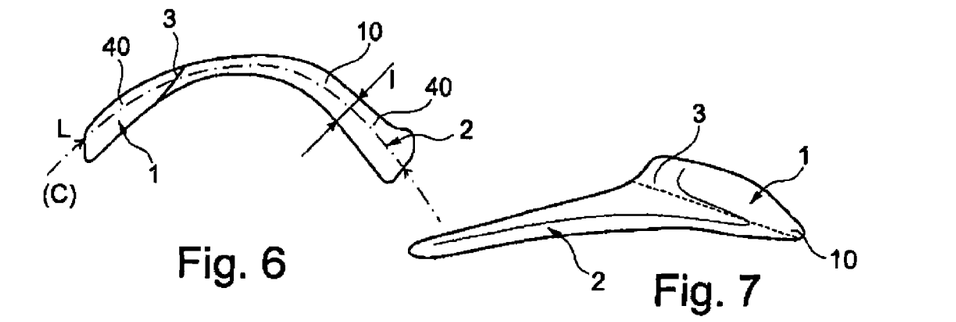
FIG. 6 illustrates another example of a membrane.
FIG. 7 represents in perspective an exemplary embodiment of a prosthesis.

In the exemplary embodiment illustrated in FIG. 6, the prosthesis 10 comprises a first portion 1 designed to mask the hollow portion of the eyelid and a second portion 2 designed to be applied to the upper eyelid. These two portions are separated by an articulation 3 corresponding for example to a zone of increased deformability or to a fold.

The prosthesis may comprise a membrane of arched shape corresponding, after the application to the eyelid, to the visible portion of the first portion and of the second portion.

In general, the prosthesis may be proposed to the user with a predefined shape or, as a variant, the user cuts the membrane. The prosthesis may have a length L, measured along its long curvilinear axis C, of between 2 and 3 cm, a greatest width I, measured perpendicularly to its long axis C, of between 3 and 10 mm. The prosthesis may have an UI ratio of between 2 and 10. The membrane and/or the entire prosthesis may be packaged pre-cut.

In the presence of such a membrane prosthesis, the first portion 1 is positioned on the hollow of the eyelid close to the medial canthus, without causing the hollow to closely follow the membrane, then the second portion 2 is placed on the movable eyelid and it is possible to carry out make-up. The whole element gives an effect of spectacular rejuvenation.

The first portion may be limited to a membrane that extends above the hollow portion without filling it or filling it only partially.

The first portion may comprise, in addition to the membrane, a malleable material, a non-malleable material or, a pasty fluid compound covered by the membrane and designed to be placed in the hollow of the eye, this material totally or partially filling the hollow portion.

If the prosthesis protrudes over the movable eyelid, it is preferable to choose to make the prosthesis of a material that is sufficiently flexible so as not to hamper the mobility of the eyelid. Moreover, the prosthesis preferably comprises an articulation 3, notably connecting the first portion 1 and the second portion 2 as illustrated also in the example of an extended prosthesis 10 illustrated in FIG. 7. The articulation 3 makes for easier movements of the movable eyelid m, once the prosthesis is in place.

Figure 8A:
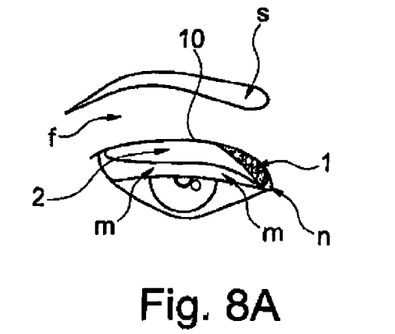
FIGS. 8A, 8B, 9A, and 9B illustrate from the front various embodiments of the prostheses after placement on the eyelid.

FIG. 8A illustrates, with the eyelid down, the placement of the prosthesis 10, the second portion 2 resting on the top of the movable eyelid m of the right eye. The prosthesis 10 is applied when the upper movable eyelid is lowered. This prosthesis is an extended prosthesis and extends beyond the filling of the hollow portion in order to cover another zone of the eyelid in addition.

An extended prosthesis may also cover the top of the nose, in a variant not illustrated.

The prosthesis 10 may be held in place on the movable upper eyelid with or without the use of an adhesive, or with the use of a wetting product, for example a moisturizing cream or a gel.

The second portion helps to hold the prosthesis by having a larger adhesive surface.

Figure 8B:
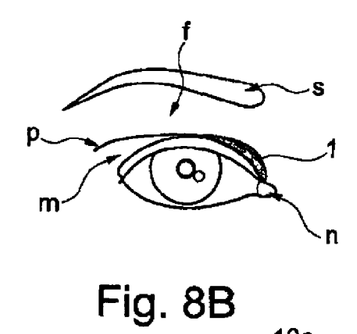

The advantage of a prosthesis that rests on the top of the movable eyelid m is that in the position with the movable eyelid raised, as illustrated in FIG. 8B, the prosthesis 10 is not seen very much at all and in particular the second portion 2 disappears in the palpebral fold p.

Figure 9A:
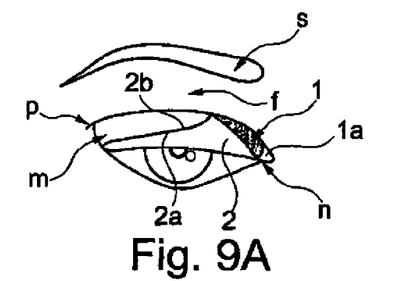
Figure 9B:
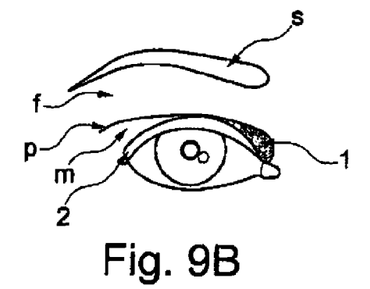

In the exemplary embodiment illustrated with the upper eyelid lowered and the eyelid raised in FIGS. 9A and 9B, the second portion rests on the bottom of the movable eyelid. Although, in this embodiment, the prosthesis is more visible than that illustrated in FIGS. 8A and 8B when the eyelid is in the raised position, the visibility of the prosthesis is limited due to the presence of the eyelashes. This configuration is of special value for the treatment of the most marked cases and in particular those that have a recess. This configuration then makes it possible to at least partially mask the recess. Preference should be given in this case to the prostheses having a certain thickness over the whole of their length.

Thus, the first portion 1 may have, as in the example illustrated, a thickness of between 40 µm, in the portion 1a nearest to the medial canthus n, and 500 µm for the larger part of this first portion. The second portion 2 is made with a membrane 40 with a thickness of between 200 µm in its central part 2a and 40 µm along the upper edge 2b.

FIGS. 10A to 10H correspond to various views of prostheses for the right eye or left eye, seen on the side of the application face.

Figure 10A:
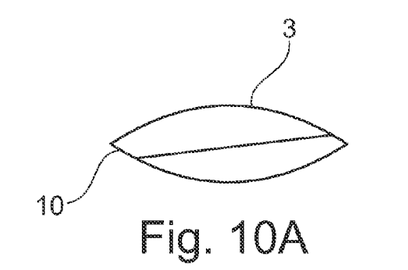
FIGS. 10A to 10H represent other forms of prostheses.

FIG. 10A corresponds to an example in which a prosthesis has been made for only the right eye.

Figure 10B:
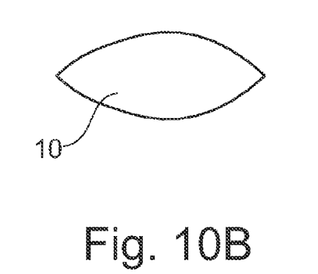
Figure 10C:
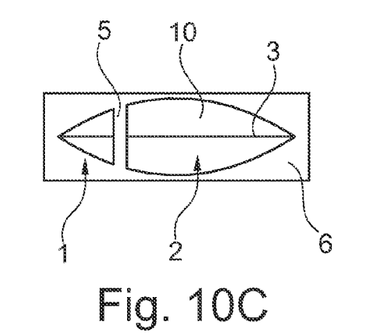

FIGS. 10B and 10C correspond to the prosthesis for the left eye and for the right eye of one and the same user: these prostheses are not symmetrical. The right prosthesis illustrated in FIG. 10C has a gap 5 between the first portion 1 and the second portion 2 corresponding to a zone in which the skin is not covered. The space created prevents the second portion 2, once the prosthesis is in place, from having folds, during certain movements of the movable upper eyelid, that folds the skin.

Before the prosthesis is placed on the eyelid, the first portion 1 and the second portion 2 are placed with precision on a guidance portion 6 made in this instance in the form of a removable strip.

The prosthesis is placed by using the guidance portion, by beginning, for example, with the first portion, then applying it gradually up to the outer corner of the palpebral fold. The prosthesis remains stuck on the eyelid after the guidance portion 6 has been removed.

Figure 10D:
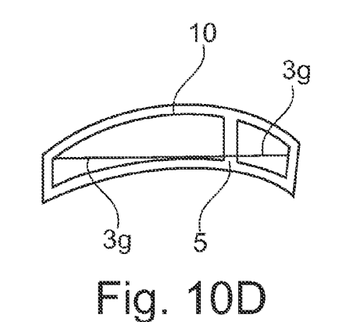

The guidance portion 6 is for example rectangular as in the example illustrated in FIG. 10C or may have any shape chosen to make placement easier, notably a shape corresponding to the general shape of the prosthesis as illustrated in FIG. 10D. The first portion 1 and the second portion 2 of the prosthesis illustrated in FIG. 10C comprise a longitudinal articulation 3.

Figure 10E:
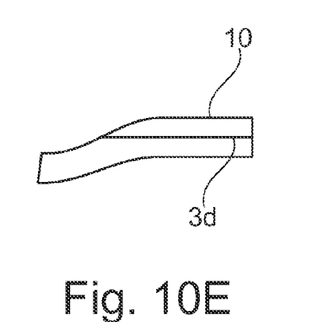

FIGS. 10D and 10E correspond to another example of left and right prostheses. The two prostheses illustrated are not symmetrical between the right eye and the left eye. They have articulations 3g and 3d in order to make movement of the movable eyelid easier.

Figure 10F:
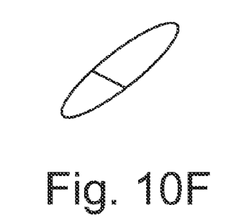
Figure 10G:
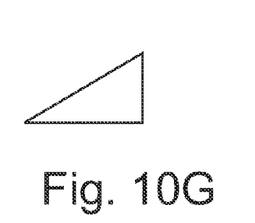
Figure 10H:
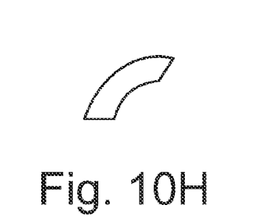

Depending on the corrections to be made, it may be of particular value to juxtapose several prostheses on the eyelid. FIGS. 10F and 10G therefore illustrate additional parts of a prosthesis that can be added to the shapes illustrated in FIGS. 10D, 10E and 10H.

EXAMPLES

The content ratios are by weight.

Example 1

Prosthesis in the adhesive paste placed in a thick layer.
The paste is a reactive silicone with the following composition:

| | |
|---|---|
| isononyl isononoate | 50 |
| phase (A) | 25 |
| phase (B) | 25 |

Phases A and B are prepared by the company Dow Corning according to the following formulae:
Phase A:

| Ingredient (INCI name) | CASE number | Content (%) | Function |
|---|---|---|---|
| Dimethylsiloxane, dimethylvinylsiloxy-terminal | 68083-19-2 | 55-95 | Polymer |
| Silica silylate | 68909-20-6 | 10-40 | Filler |
| 1,3-Diethenyl-1,1,3,3-tetramethyldisiloxane complexes | 68478-92-2 | Trace | Catalyst |
| Tetramethyldivinyldisiloxane complex | 2627-95-4 | 0.1-1 | Polymer |

Phase B:

| Ingredient (INCI name) | CASE number | Content (%) | Function |
|---|---|---|---|
| Dimethylsiloxane, dimethylvinylsiloxy-terminal | 68083-19-2 | 55-95 | Polymer |
| Silica silylate | 68909-20-6 | 10-40 | Filler |
| Dimethyl, Methylhydrogen Siloxane, trimethylsiloxy-terminal | 68037-59-2 | 1-10 | Polymer |

It is possible to make provision to add pigments, for example coated iron oxide from the company ITT, at 3% content by weight, while reducing the content of isononyl isononoate.
Operating Mode
The pigments, when they are present, are ground in the tri-cylinder in the isononyl isononoate.
Phase A and the pigment phase are mixed in a 10 ml flask and homogenized in the vortex. Then phase B is added and homogenized in the vortex.

Spread immediately with the aid of a spatula in the hollow of the eye.
The material dries in 5 minutes. The prosthesis adheres well, is not very visible, in particular once it is made up. The prosthesis obtained may therefore stay in place for quite a long time and is easily removed thereafter.

Example 2

In another example, an adhesive compound containing a polyester sulfonate polymer is first applied to a portion of the eyelid. It is possible, for example, to choose the compound AQ 1350 from Eastman Chemicals used pure.
After application, repeat the same test as example 1.

Example 3

Carry out the same test as in examples 1 or 2. After application, apply a talcum powder with a brush. The material has a dry appearance when the talc has been applied.

Example 4

Cut a membrane according to the embodiment illustrated in FIG. 6.
The first portion 1 is placed on the hollow of the eyelid close to the medial canthus without causing the hollow to closely follow the membrane and then the second portion 2 is placed on the movable eyelid and make-up is applied.

Example 5

As illustrated in FIG. 5, cut a membrane 40 from a Tegaderm adhesive film with an ovoid shape 5 mm high and 10 mm long.
Then place on the film, in its adhesive part, 20 mg of pasty fluid compound 60 according to the formula of example 1.
The invention is not limited to the examples illustrated, for example, the prosthesis may be made with yet other shapes.
The expression "comprising one" is synonymous with "comprising at least one", unless specified to the contrary.

The invention claimed is:

1. A cosmetic method for temporary modification of an appearance of a contour of an eye, the method comprising:
   placing an aesthetic prosthesis at least on a hollow portion of an upper eyelid, wherein the hollow portion is situated close to a medial canthus,
   wherein the placing includes visually and/or physically filling at least a portion of the hollow portion with at least a first portion of the aesthetic prosthesis, and
   wherein the aesthetic prosthesis comprises at least one elastic membrane and a malleable material.

2. The method according to claim 1, wherein the first portion comprises a malleable material.

3. A cosmetic method for temporary modification of an appearance of a contour of an eye, the method comprising:
   placing an aesthetic prosthesis at least on a hollow portion of an upper eyelid, wherein the hollow portion is situated close to a medial canthus,
   wherein the placing includes visually and/or physically filling at least a portion of the hollow portion with at least a first portion of the aesthetic prosthesis, and
   wherein the first portion comprises a cavity.

4. The method according to claim 1, wherein the first portion comprises as a closed cavity.

5. The method according to claim 1, wherein the first portion comprises a sealed cavity.

6. The method according to claim 3, wherein the cavity contains a fluid at least before the prosthesis is put in place.

7. The method according to claim 1, wherein the first portion contains a substance at least before the prosthesis is placed in the hollow portion.

8. A cosmetic method for temporary modification of an appearance of a contour of an eye, the method comprising:
 placing an aesthetic prosthesis at least on a hollow portion of an upper eyelid, wherein the hollow portion is situated close to a medial canthus,
 wherein the placing includes visually and/or physically filling at least a portion of the hollow portion with at least a first portion of the aesthetic prosthesis, and
 wherein the first portion contains a substance at least before the prosthesis is placed in the hollow portion and the substance is a paste.

9. A cosmetic method for temporary modification of an appearance of a contour of an eye, the method comprising:
 placing an aesthetic prosthesis at least on a hollow portion of an upper eyelid, wherein the hollow portion is situated close to a medial canthus,
 wherein the placing includes visually and/or physically filling at least a portion of the hollow portion with at least a first portion of the aesthetic prosthesis, and
 wherein the first portion contains a substance at least before the prosthesis is placed in the hollow portion and the substance is reticulatable.

10. A cosmetic method for temporary modification of an appearance of a contour of an eye, the method comprising:
 placing an aesthetic prosthesis at least on a hollow portion of an upper eyelid, wherein the hollow portion is situated close to a medial canthus,
 wherein the placing includes visually and/or physically filling at least a portion of the hollow portion with at least a first portion of the aesthetic prosthesis, and
 wherein the first portion contains a substance at least before the prosthesis is placed in the hollow portion and the substance is a fluid.

11. The method according to claim 1, wherein the prosthesis comprises a second portion connected to the first portion by an articulation mechanism.

12. The method according to claim 1, wherein the prosthesis comprises a second portion that is configured to detach from the first portion.

13. The method according to claim 1, wherein the prosthesis comprises a second portion connected to the first portion, wherein the second portion is degradable.

14. The method according to claim 13, wherein the second portion is degradable by being dissolved in solvent.

15. The method according to claim 1, wherein the prosthesis further comprises a guidance portion, wherein at least during a step of placing the prosthesis, the guidance portion extends over the whole eyelid and/or a portion of the nose.

16. A cosmetic method for temporary modification of an appearance of a contour of an eye, the method comprising:
 placing an aesthetic prosthesis at least on a hollow portion of an upper eyelid, wherein the hollow portion is situated close to a medial canthus,
 wherein the placing includes visually and/or physically filling at least a portion of a space defined by the hollow portion with at least a first portion of the aesthetic prosthesis, and
 wherein the prosthesis comprises at least one elastic membrane and a non-malleable material.

17. A cosmetic method for temporary modification of an appearance of a contour of an eye, the method comprising:
 placing an aesthetic prosthesis at least on a hollow portion of an upper eyelid, wherein the hollow portion is situated close to a medial canthus,
 wherein the placing includes visually and/or physically filling at least a portion of the hollow portion with at least a first portion of the aesthetic prosthesis, and
 wherein the prosthesis comprises at least one elastic membrane and a paste.

18. The method according to claim 1, wherein the prosthesis comprises a first and a second elastic membrane and a substance placed between the membranes.

19. The method according to claim 1, wherein a maximum thickness of the first portion is greater than or equal to 300 µm.

20. The method according to claim 1, wherein the maximum thickness of the first portion ranges from 500 µm and 5 mm.

21. The method according to claim 1, further comprising, prior to the placing of the prosthesis, cutting and/or fashioning the first portion.

* * * * *